United States Patent [19]
Komesaroff

[11] Patent Number: 5,566,669
[45] Date of Patent: Oct. 22, 1996

[54] AUTOCLAVABLE CARBON DIOXIDE ABSORBER/VALVE FOR USE IN ANESTHESIA AND RESUSCITATION APPARATUS

[75] Inventor: David Komesaroff, Melbourne, Australia

[73] Assignee: Techbase Pty Ltd., Melbourne, Australia

[21] Appl. No.: 490,779

[22] Filed: Jun. 15, 1995

[30] Foreign Application Priority Data

Jun. 20, 1994 [AU] Australia .................. PM6344

[51] Int. Cl.⁶ .............. A61M 16/20; A61M 16/22
[52] U.S. Cl. .............. 128/205.12; 128/205.24; 128/204.28; 128/205.14; 128/205.13; 128/205.28; 128/909
[58] Field of Search ............. 128/204.28, 205.12, 128/205.13, 205.14, 205.17, 205.27, 205.28, 909, 910, 205.29

[56] References Cited

U.S. PATENT DOCUMENTS

| | | | |
|---|---|---|---|
| D. 253,721 | 12/1979 | Gibeck | D24/52 |
| D. 301,377 | 5/1989 | Lambert | D24/52 |
| 2,586,670 | 2/1952 | Lambertsen | 128/205.29 X |
| 3,566,867 | 3/1971 | Dryden | 128/188 |
| 3,575,167 | 4/1971 | Michielsen | 128/205.28 |
| 3,615,233 | 10/1971 | Doering | 128/205.28 X |
| 3,700,000 | 10/1972 | Vesse et al. | 137/494 |
| 3,738,360 | 6/1973 | Dryden | 128/188 |
| 3,752,186 | 8/1973 | Dryden | 137/608 |
| 3,830,632 | 8/1974 | Guzay | 128/205.28 X |
| 3,835,627 | 9/1974 | Dryden | 55/387 |
| 3,926,458 | 12/1975 | Dryden | 285/177 |
| 3,960,148 | 6/1976 | Dryden | 128/188 |
| 4,232,667 | 11/1980 | Chalon et al. | 128/203.26 |
| 4,350,662 | 9/1982 | Dowgul et al. | 422/122 |
| 4,791,922 | 12/1988 | Linsay-Scott et al. | 128/205.28 |
| 4,838,258 | 6/1989 | Dryden et al. | 128/204.18 |
| 5,033,464 | 7/1991 | Dlcastilho | 128/205.19 |
| 5,042,468 | 8/1991 | Lambert | 128/200.26 |
| 5,284,160 | 2/1994 | Dryden | 128/203.12 |
| 5,320,096 | 6/1994 | Hans | 128/205.29 |
| 5,462,048 | 10/1995 | Lambert et al. | 128/201.13 |

FOREIGN PATENT DOCUMENTS

| | | | |
|---|---|---|---|
| 628643 | 5/1961 | Canada | 128/205.28 |
| 653216 | 5/1951 | United Kingdom | 128/205.28 |
| 92/20404 | 11/1992 | WIPO | 128/205.28 |

*Primary Examiner*—V. Millin
*Assistant Examiner*—Eric P. Raciti
*Attorney, Agent, or Firm*—Bose McKinney & Evans

[57] ABSTRACT

A canister (10) is provided for use with an anaesthesia and resuscitation machine. The canister (10) includes a canister body (12) defining an interior (41) for holding carbon dioxide absorbent (114). A unidirectional expiratory valve (40) is integrally mounted to the canister body (12) through which a patient gas can pass into the canister body interior (41), and a unidirectional inspiratory valve (42) is provided through which the patient gas can pass out of the canister body interior (41). An overflow orifice (102) extends through the canister body, through which the patient gas can pass. A unidirectinal overflow valve (150) is coupled to the overflow orifice (102) for permitting a controlled flow of patient gas therethrough to maintain the desired patient gas pressure within the interior (41) of the canister body (12). When the valve (150) is in its unlocked position, it is normally biased by gravity into a valve engaged position to automatically adjust the flow of excess patient gas therethrough, by being moveable under the influence of gas pressure within the canister into a valve disengaged position. In the valve disengaged position, patient gas can pass through the overflow valve (150). Also, the valve (150) can be locked in the valve engaged position.

22 Claims, 8 Drawing Sheets

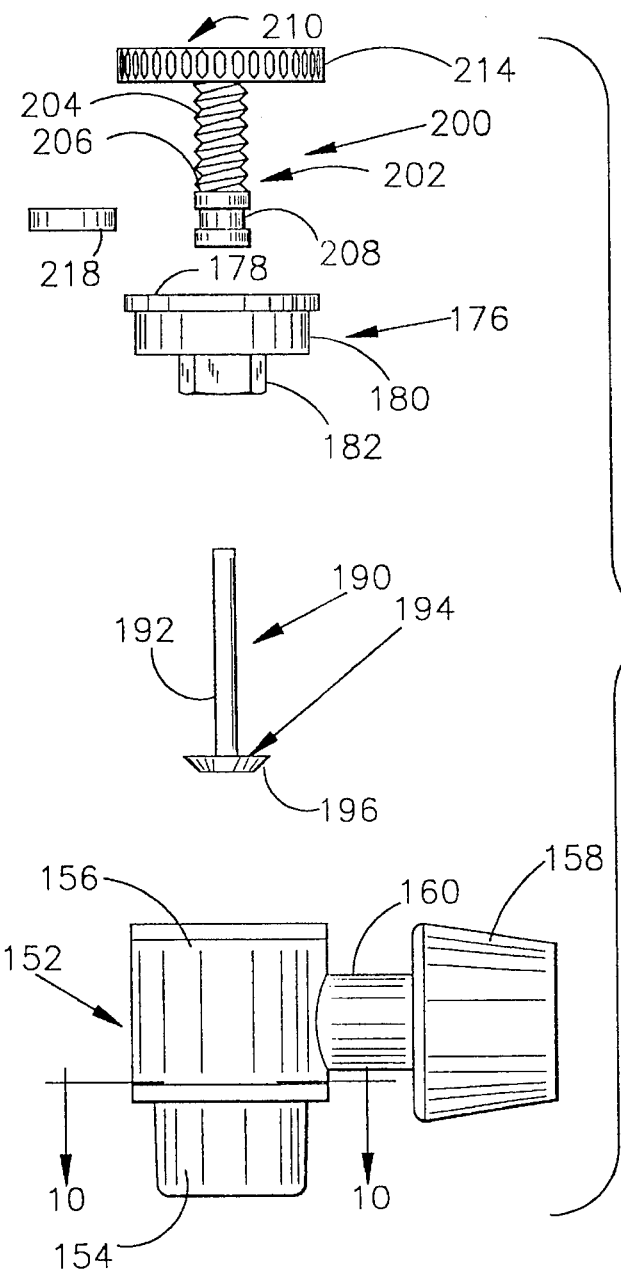
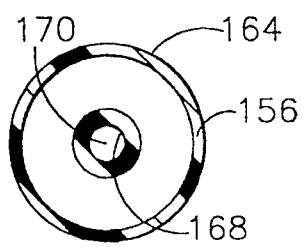
FIG. 10
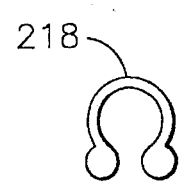
FIG. 9

AUTOCLAVABLE CARBON DIOXIDE ABSORBER/VALVE FOR USE IN ANESTHESIA AND RESUSCITATION APPARATUS

TECHNICAL FIELD OF THE INVENTION

The present invention relates to anaesthesia equipment and more particularly to an autoclavable or single use disposable carbon dioxide absorber (canister) and associated valve system for use with anesthesia and resuscitation machines.

BACKGROUND OF THE INVENTION

A major problem with current carbon dioxide absorber equipment is the difficulty (in some cases impossibility) experienced in achieving adequate heat autoclaving particularly if this is to be done after each patient use. Conventional equipment is fixed or semi-fixed and has not been designated to be easily dismantled and re-assembled with frequent straightforward autoclaving procedures in mind.

Conventional equipment typically includes a soda lime canister with separate valves. Such equipment need to be dismantled for autoclaving, and therefore is often not autoclaved between patients.

Additionally, many conventional canisters are bulky and heavy and therefore are usually only autoclaved on an infrequent basis. Also, some or all of the other components including metal and composite metal/plastic unidirectional and overflow valves (sometimes called adjustable pressure limiting (APL) valves), and fixed connecting parts bolted to the anaesthetic machine cannot be autoclaved without great difficulty and consequently autoclaving of these parts is rarely done.

Apart from the valves and absorber, the breathing circuit includes breathing hoses, a Y-piece or equivalent connector and a face mask, all of which should be readily autoclaved or replaced by single use equipment.

It is also known to provide single use absorbers or autoclavable plastic absorbers which can be removed or replaced as a single use device. However, the various associated equipment including unidirectional valves and/or an exhaust valve with or without a scavenging port are, in fact, separate pieces of equipment and do not form an integral part of the canister body.

An example of a known, single use carbon dioxide absorber device is the ISO-GARD $CO_2$ ABSORBER SYSTEM manufactured by GIBECK-DRYDEN CORP. of Indianapolis, Ind. U.S.A. Although several known devices (including the GIBECK-DRYDEN device) most likely perform their intended function in a workmanlike manner, room for improvement exists. One area in which room for improvement exists is in the adjustability of known overflow valves. It is difficult to properly adjust the flow rate of gasses through the overflow valve in some known devices because it has been the Applicant's experience that the devices do not respond well to fine adjustments. This problem is especially acute at the low gas flow rates (e.g., 1or 2liters per minute) that are now being used more frequently.

The present invention has as one of its objectives the provision of a carbon dioxide absorber and integrated valve system for use with anaesthetic and resuscitation equipment which can easily be made portable, be easily dismantled from the equipment for sterilization and in some forms can be disposable for one off use.

Furthermore, it is an objective to provide an improved adjustable pressure limiting valve in such equipment for closely controlling the outflow of excessive gas in the circuit but yet automatically enables the breathing bag to be maintained in a normal inflated condition, particularly when used in patients breathing spontaneously.

SUMMARY OF THE INVENTION

In accordance with the present invention, a canister is provided for use with an anaesthesia and resuscitation machine. The canister includes a canister body defining an interior for holding a carbon dioxide absorbent material. A unidirectional expiratory valve is integrally mounted to the canister body through which a patient gas can pass into the canister body interior, and a unidirectional inspiratory valve is provided through which the patient gas can pass out of the canister body interior. An overflow orifice extends through the canister body, through which the patient's excess gas can pass, and a one-way overflow valve is coupled to the overflow orifice for permitting a controlled flow of patient gas therethrough to maintain a desired gas pressure within the interior of the canister body. When the valve is in its unlocked position, it is biased by gravity into a valve engaged position.

Preferably, the valve means includes a valve actuating means for adjusting the valve between a locked position and an unlocked position. In the locked position, the valve member is locked into a valve engaged position where the valve member is engaged with the valve seat to prevent the flow of patient gas through the valve aperture. In the unlocked position, the valve member can move, under the influence of patient gas pressure, and against the influence of gravity, between a valve engaged position and a valve disengaged position. In the valve disengaged position, the valve member is disposed in a spaced relation to the valve seat to permit the patient gas to flow through the valve aperture. Preferably, the valve is adjustable to permit a variable flow rate through the aperture. Also, when the valve is in its unlocked position, the valve member is biased by gravity into its engaged position.

One feature of the present invention is that the overflow valve (in its unlocked position), is designed to be gravity biased into its valve engaged position, rather than spring biased. This feature has the advantage (in patients breathing spontaneously) of enabling the valve to operate well, without manual adjustment, over the range of gas flow rates commonly used in anaesthesia and resuscitation. This represents a vast improvement over some known devices which require constant manual adjustment during a procedure to match the flow rates with the patient's needs. As will be appreciated, the gas flow rate delivered to a patient during a procedure will often vary during the procedure. These changes in gas delivery flow rates often require frequent adjustments of the overflow valve of prior art devices. The present invention reduces the need to make these adjustments in the overflow valve during procedures.

The valve element which comprises the moving part of the valve is preferably designed to be of light weight, but to have sufficient mass to allow a slight positive pressure in the breathing circuit to exist, to thereby ensure that a breathing bag attached to the canister is maintained in an inflated state when the valve is placed in its unlocked position at all flow rates, even with the currently preferred low inflow and ventilation rates.

Another feature of the present invention is that the canister is constructed so that the integrated unidirectional inspiratory and expiratory valves, and the overflow valves are sealed to become a single unit, so that the canister can be separated easily from the main anaesthetic and resuscitation machine for disposal (disposable version) or for autoclaving (autoclavable version) as appropriate. The autoclavable version of the canister can also include a fill port to enable convenient emptying and refilling with fresh soda lime after each use.

A further feature of the present invention is that a breathing bag cavity is provided to which a breathing bag can be attached. The breathing bag cavity is disposed both downstream and upstream from the absorbent cavity, so that the patient gas must pass through one part of the absorbent before entering the breathing bag cavity, and also pass through another part of the absorbent after leaving the breathing bag cavity, and before entering the inspiratory cavity. This feature has the advantage of causing a large part of the patient gas to pass through the carbon-dioxide-removing absorbent twice before being returned to the patient. This double pass helps to ensure a more complete removal of the carbon dioxide from the patient gas, and helps to increase the efficiency of the device.

Another feature of the present invention is that the grates through which patient gas can pass into the absorbent cavity from each of the expiratory cavity and the breathing bag cavity are beveled, so that the grate openings on one side of the grate are smaller than those on the other side of the grate. In one embodiment, the grate openings adjacent to the absorbent cavity are preferably smaller than the openings adjacent to either of (1) the breathing bag cavity, (2) the expiratory cavity, or (3) the inspiratory cavity. This feature has the advantage of better dispersing the patient gas through the absorbent, to better ensure that the patient gas passes through the absorbent to have its carbon dioxide removed.

These and other features of the present invention will become apparent to those skilled in the art upon a review of the drawings and detailed description of the preferred embodiment of the present invention.

BRIEF DESCRIPTION OF THE DRAWINGS

FIG. 1A is a perspective view of an alternate embodiment breathing bag line designed to comply with Australian standards;

FIG. 7 is a exploded view of the valve means of the present invention;

FIG. 9 is a top view of a retainer ring associated with the valve means of the present invention;

FIG. 10 is a sectional view taken along lines 10—10 of FIG. 7; and

DETAILED DESCRIPTION OF PREFERRED EMBODIMENTS

Figure 1:
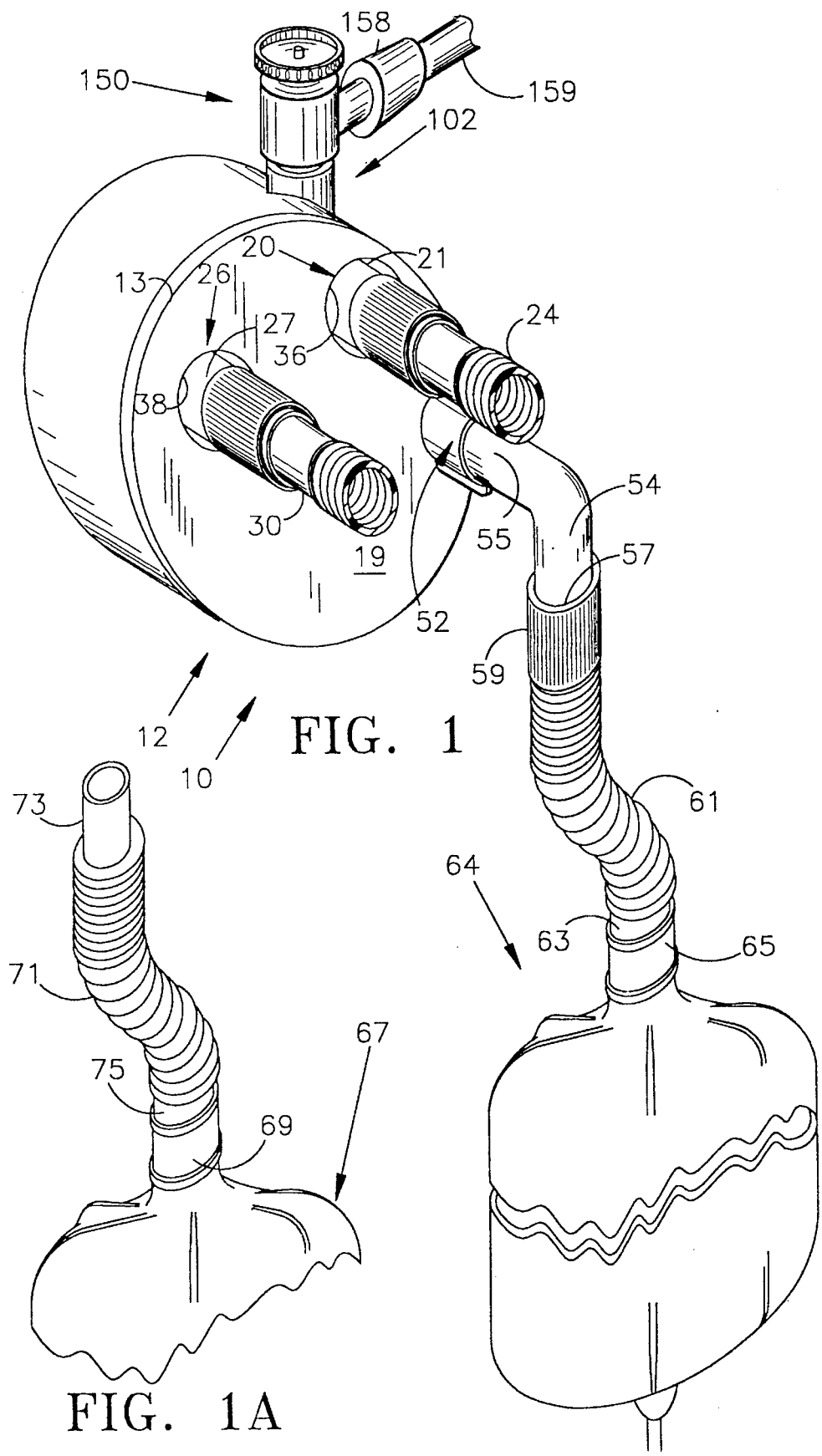
FIG. 1 is a perspective view showing the canister of the present invention in connection with the various gas lines and breathing bag hose lines typically associated therewith during normal use.
Figure 3:
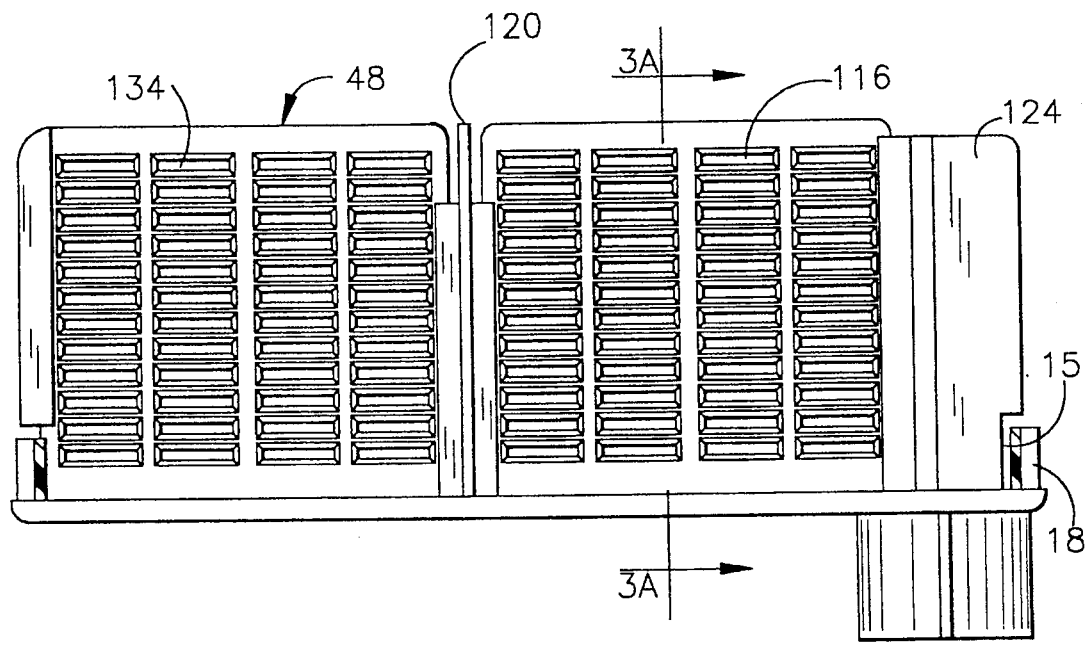
FIG. 3 is a sectional view taken along lines 3—3 of FIG. 2.

Canister 10 of the present invention for containing a carbon dioxide absorbent, such as soda lime is shown in FIG. 1. The canister 10 includes a canister body 12 having a bowl portion 14 having a generally straight-sided cylindrical sidewall 13 which terminates at its upper end in a circumferential lip 15, which is best shown in FIG. 3. The circumferential lip 15 is provided for being received snugly into a circumferential flange 18 that extends perimeterially around the generally planar top portion 19 (FIG. 4) of the lid portion 16 of the canister body 12.

The canister body 12 and all of its components (with the exception of the absorbent 114, the expiratory valve 40 and the inspiratory valve 42) are preferably constructed of a high-impact medical grade polycarbonate, which is designed to be autoclavable for at least 50 cycles at about 137° C. The material chosen and the thickness and strength of the various components should be such to make the device shock resistant to damage, so that if the device is dropped or otherwise impacted during use, it will not be likely to break, crack or leak. Alternately, the material from which the canister 10 can be made can be "less sturdy" (e.g., polystyrene) and, therefore, less expensive to manufacture if the canister 10 is designed to be disposed after one use.

The top portion 19 of the lid 16 includes an expiratory line receiving station 20 which includes an expiratory port 21 that is formed integrally with the top portion 19. The expiratory port 21 is provided for being received by an expiratory line 24. The expiratory port 21 includes a key portion 23 (which is absent in the inspiratory port 27) that prevents the insertion of a 15 mm. connection which is sometimes used for insertion into the inspiratory port. This expiratory line 24 extends, ultimately to a face mask of a patient, and is provided for carrying expiratory patient gas that is exhaled by the patient to the canister 10.

An inspiratory line receiving station 26 is also provided on the top portion 19 of the lid 16, and includes an inspiratory port 27 that is formed integrally as a part of the top portion 19 of the lid 16. The inspiratory port 27 is provided for being received by, and coupled to a female coupler of an inspiratory line 30. Inspiratory line 30 extends eventually to the face mask of a patient, and is provided for carrying inspiratory patient gas from the canister 10, to the patient, for being inhaled by the patient. Unlike expiratory port 21, inspiratory port 27 contains no key portion (e.g., 23), as certain procedures use a 15mm male coupling member that is inserted into, and received by the inspiratory port 27.

As will be appreciated, inspiratory line 30 and expiratory line 24 can both be part of a single Y-type connector, which feeds the respective streams of gas into a coaxial breathing circuit. An example of a coaxial breathing circuit is the UNIVERSAL F® Breathing Circuit manufactured by King Systems Corporation of Noblesville, Ind, which is disclosed in Leagre and Burrow U.S. Pat. No. 5,404,873. In such a case, the Y-connection is designed to segregate the expiratory patient gas from the inspiratory patient gas so that the two gas streams are mixed only at the face mask, or at a connector adjacent to the face mask. A description of a manner in a coaxial breathing circuit segregates the expiratory and inspiratory patient gasses is presented in the above referenced Leagre et al. U.S. Patent.

Figure 4:
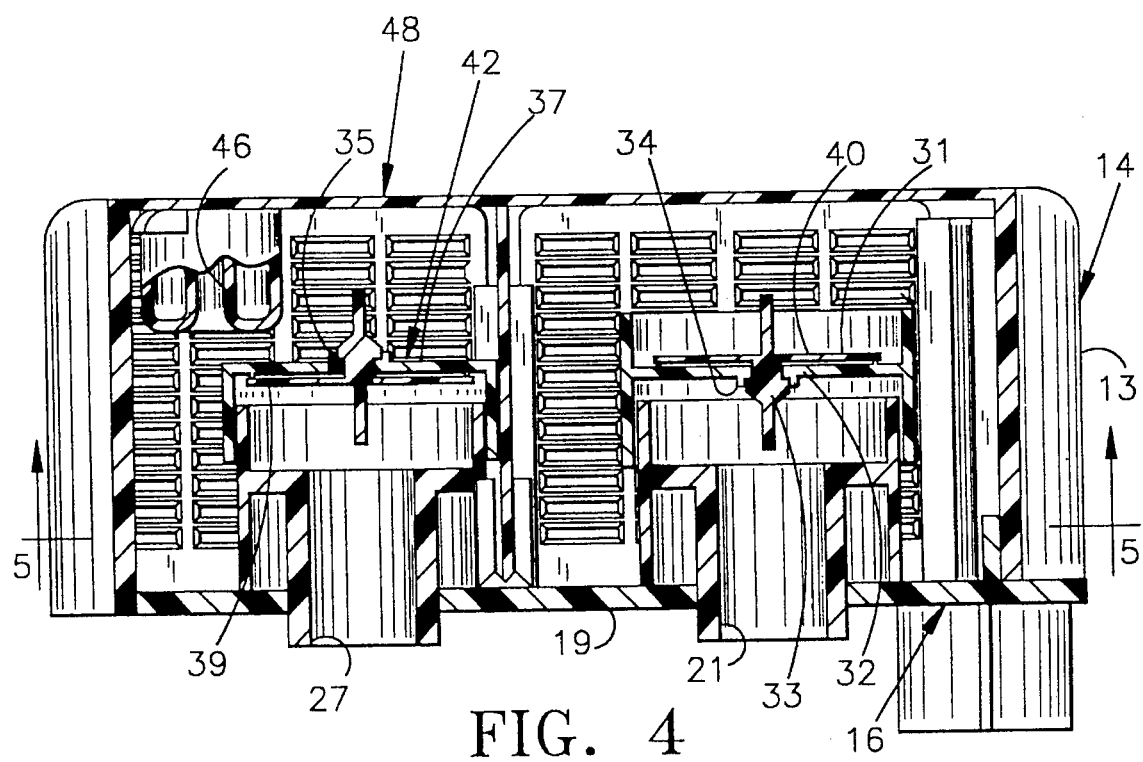
FIG. 4 is a sectional view taken along lines 4—4 of FIG. 2.

A bowl-like expiratory dish 36 and inspiratory dish 38, surround the respective expiratory port 21 and inspiratory port 27. The expiratory and inspiratory dishes 36, 38 provide a barrier between the exterior of the canister body 12, and the interior thereof. As best shown in FIG. 4, a unidirectional expiratory valve 40 is coupled to the expiratory dish 36, and is provided for permitting patient gas to flow from the expiratory port 21 into the interior 41 of the canister body 12. As best shown in FIG. 4, unidirectional expiratory valve 40 allows patient gas to flow into, but not out of, the interior 41 of the canister body 12. A unidirectional inspiratory valve 42 is coupled to the inspiratory dish 38, and allows patient gas to flow only from the interior 41 of the canister body 12, out through the inspiratory port 27, while preventing the flow of patient gas from the inspiratory port 27 into the interior 41 of the canister body 12.

The expiratory valve 40 comprises a circular, disk-like silicon valve leaflet 31 having a perpendicular probe portion 33 which is captured in a central aperture formed in a valve seat member 32. The valve seat member 32 includes axially extending protrusions 34 which help to prevent improper assembly of the leaflet 31 to the seat 32, by permitting the probe portion to be inserted into the aperture only from one direction. Unidirectional inspiratory valve 42 is generally similar in construction to expiratory valve 40, except that the protrusions 35, valve leaflet 39 and probe portion 44 are placed on the opposite side of valve seat 37.

A fresh gas inlet port 46 is integrally formed on the back wall 48 of the bowl portion 14 of the canister body 12. The fresh gas inlet port 46 can be coupled to either a straight tube connector (not shown) or else to an elbow tube connector 68, and a fresh gas line 70. The fresh gas line 70, elbow connector 68, and fresh gas inlet port 46 enable the physician to direct a stream of fresh anaesthesia gas into the interior 41 of the canister body 12. The fresh gas inlet port 46 is disposed adjacent to the unidirectional inspiratory valve 42, and downstream of the soda lime absorbent 114 contained within the interior 41 of the canister body 12, so that the fresh gas flowing from the fresh gas inlet port 46 is directed out to the patient through the inspiratory port 27, without being absorbed, trapped or chemically altered by the carbon dioxide absorbent material 114 contained within the interior 41.

Figure 2:
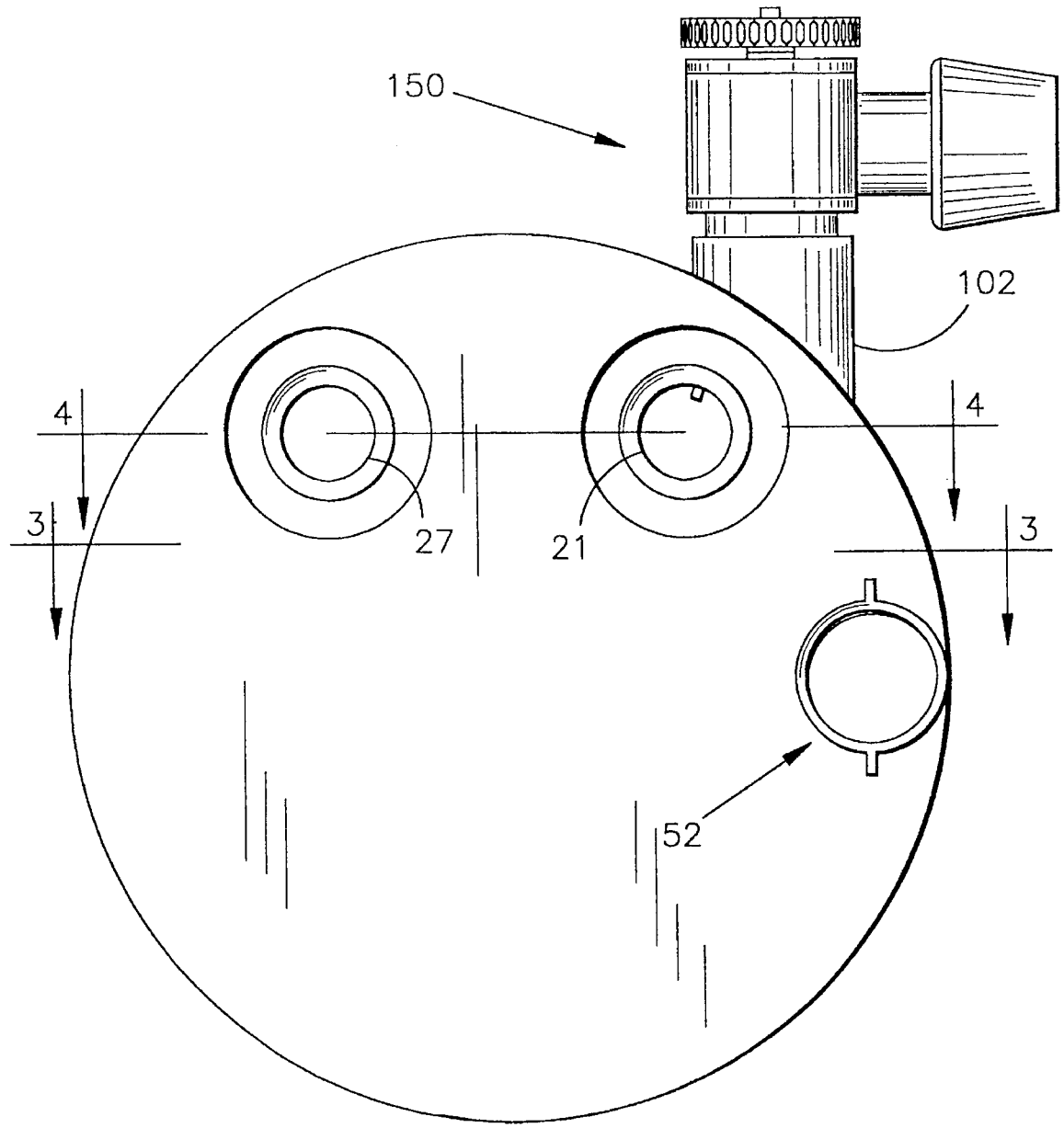
FIG. 2 is a front view of the canister of the present invention with the associated lines removed.

As best shown in FIG. 2, a breathing bag port 52 is integrally formed as a part of the top portion 19 of the lid 16. The breathing bag port 52 can be coupled to an elbow connector 54. Elbow connector 54 preferably has 22 mm. male fittings at each end. To comply with relevant American and ISO standards, the first end 55 of the elbow connector 54 should be bonded permanently to breathing port 52, so that breathing bag port 52 effectively becomes a male 22 mm. fitting due to the unattached second end 57 of the elbow connector 54. As shown in FIG. 1, the second end 57 of the male-male elbow connector 54 is received by a female connector 59 mounted to a first end of a breathing bag hose line 61. The male second end 63 of the breathing bag hose line 61 is received within the interior of the female coupling port 65 of the breathing bag 64. However, the elbow port 54 should not be permanently bonded to those canisters intended for sale in the Australian market. Turning now to FIG. 1A, the Australian market also uses a conventional breathing bag 67 having a female connector port 69, but does not include a permanently bonded male-male connector (e.g. 54). As such, the breathing bag hose line 71 should have a 22mm male first end 73 for being received by breathing bag port 52, and a male second end 75 for receiving the female connector port 69 of the breathing bag 67. Preferably, male first end 73 is elbow shaped to cause breathing bag hose line 71 to extend downwardly.

The breathing bag 64 is usually maintained in an inflated state.. When the overflow valve is in the locked position, the anesthesiologist can force gas into the patient by squeezing the bag 64, and thereby forcing patient gas through inspiratory line 30 to the face mask of the patient. During a procedure, the valve 150 can be intermittently unlocked to release excess patient gas.

A fill orifice 74 is provided in the back wall 48 of the bowl portion 14, through which fresh $CO_2$ absorbent can be placed into the interior 41 of the canister body 12, and through which exhausted absorbent can be removed from the canister body 12. A removable rubber plug 76 is provided for plugging the fill orifice 74. The rubber plug 76 preferably includes an outer lip 78 which is normally disposed exteriorly of the fill orifice 74, an axially extending portion 80 which snugly grips the rim of the fill orifice 74, and an inner lip 82 which engages the inner surface of the back portion 48, to maintain the rubber plug 76 in engagement with the fill orifice 74. In the disposable model, the plug 76 and fill orifice 74 can be eliminated, and the device filled with absorbent at the factory before the lid 16 is attached to the bowl portion 14. With this type of disposable model, the entire device should be discarded after a single use.

Three recessed cavities are also formed in the back wall 48 of the bowl portion 14. Each of the three cavities comprises a dish, having a closed end. None comprises a port through which gas can flow. The three cavities include a central mounting dish 86, an upper mounting dish 88, and a lower mounting dish 90. The three mounting dishes 86–90 are provided for each receiving a stud member which is a part of the mounting bracket system (not shown) of the anaesthesia machine (not shown) used by the anesthesiologist. The studs (not shown) of the mounting bracket (not shown) extend into, and are fictionally received by one or more of the mounting dishes 86–90 for securing the canister 10 to the mounting bracket (not shown), and for fixedly positioning the canister 10 onto the mounting bracket. Preferably, the upper and lower mounting dishes 88, 90 can be threaded to receive a threaded screw as an alternative means of mounting the canister to the mounting bracket.

Figure 5:
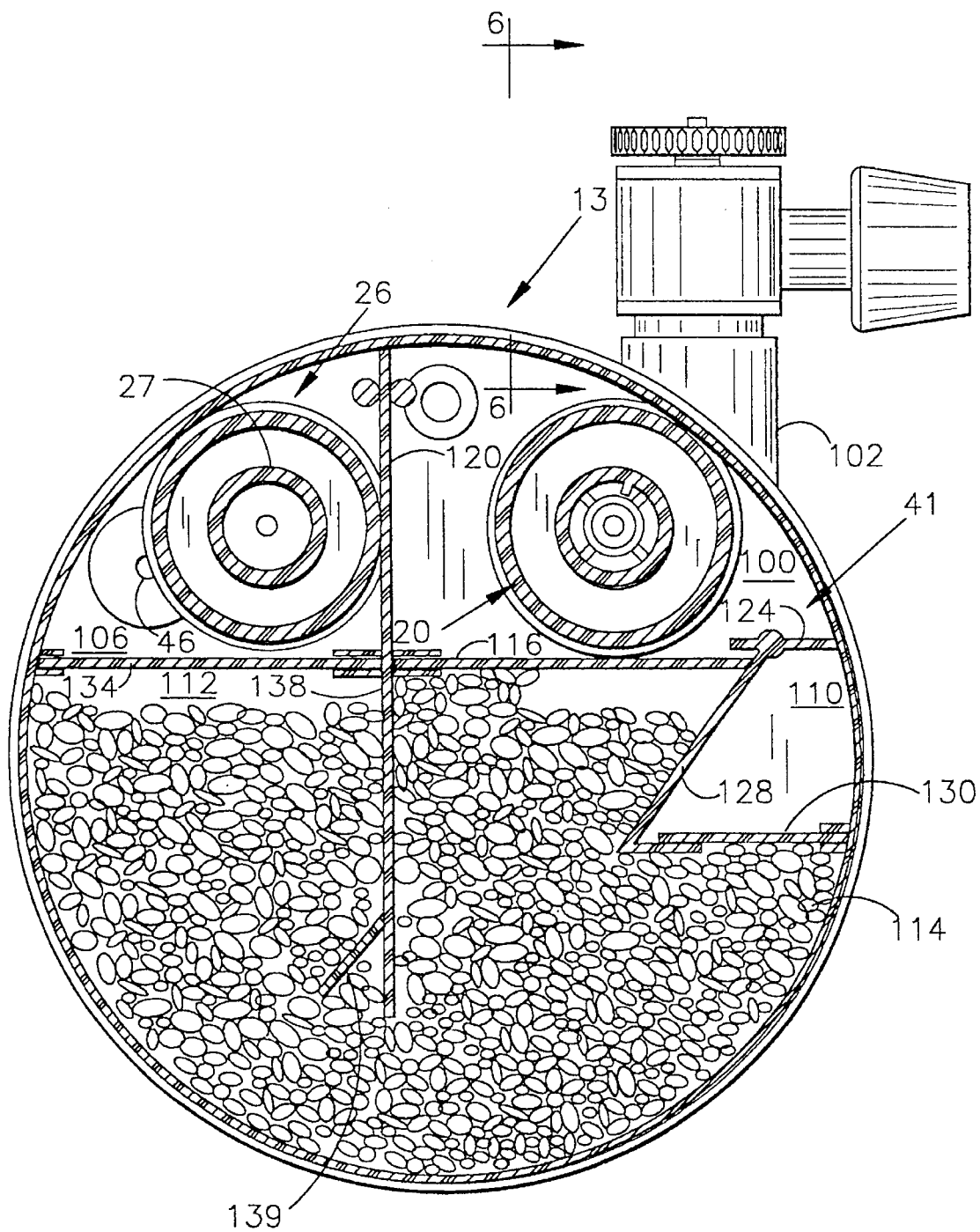
FIG. 5 is a sectional view taken along lines 5—5 of FIG. 4.

As best shown in FIG. 5, the interior 41 includes a series of partition means which define a plurality of chambers or cavities within the interior 41 of the canister 10 canister body 12. These cavities include an expiratory cavity 100, which is the cavity into which expiratory gas is directed which flows through the expiratory port 21. The expiratory cavity 100 is in fluid communication with the expiratory port 21, through the unidirectional expiratory valve 40. An overflow port 102 is formed in cylindrical wall 13 portion of the bowl portion 14 of the canister 10, and is also in fluid communication with the expiratory cavity 100.

An inspiratory cavity 106 is in fluid communication with each of the inspiratory port 27, and the fresh gas orifice 46.

The partition means further defines a breathing bag cavity 110 which is disposed adjacent to the cylindrical wall 13 of the bowl portion 14, and below the expiratory cavity 100. The breathing bag cavity 110 is in fluid communication with the breathing bag port 52, and with the absorbent cavity 112. The absorbent cavity 112 contains the largest volume of space, and is disposed generally below each of the expiratory cavity 100, inspiratory cavity 106, and breathing bag cavity 110. The absorbent cavity 112 is large enough to contain about 400 grams by weight of a soda-lime type carbon dioxide absorber.

Acceptable $CO_2$ soda-lime absorbent is available from a variety of FDA approved manufacturers and marketers. Typically, the $CO_2$ absorbent is designed to change color as it loses its capacity to absorb $CO_2$, and hence becomes used up. For example, one known brand of soda-lime is designed to be white when "fresh" and to change color to become violet when $CO_2$ is absorbed by the absorbent. Another brand is designed to be pink when fresh, and to turn white as it absorbs $CO_2$. This color change assists the anesthesiologist to keep track of the absorbent's remaining capacity to absorb carbon dioxide by providing a signal to the anesthesiologist that the absorbent capacity of the $CO_2$ absorber has been reached, thus alerting the anesthesiologist of the need for fresh absorbent.

It has been found by the applicant that the 400 grams of soda-lime which are capable of being placed in the absorbent cavity 112 provide for adequate removal of carbon dioxide for an average of 160 minutes at flow rates of 0.5 liters per minute of oxygen in conscious volunteers, and in excess of 220 minutes under conditions of anesthesia, and fresh gas flow rates of one liter per minute.

Figure 3A:
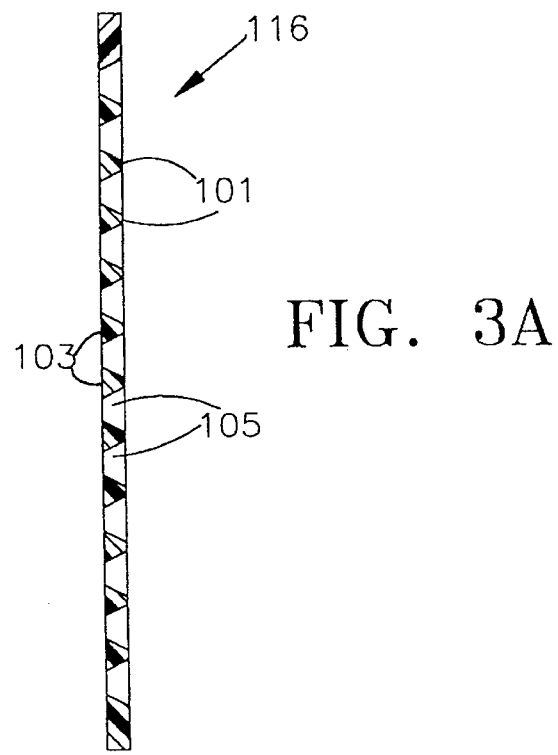
FIG. 3A is a sectional view taken along lines 3A—3A of FIG. 3.

As best shown in FIGS. 3–5, the partition means includes several portions for defining the cavities discussed above. The portions include a first grate portion 116 which extends generally horizontally between the expiratory cavity 100 and the absorbent cavity 112. The first grate portion 116 contains a large number of air passages, thereby placing the expiratory cavity 100 in fluid communication with the cavity 112. As best shown in FIG. 3A, the "grates"of the first grate are generally truncated equilateral triangles in cross section, with their apexes 101 disposed adjacent the expiratory cavity 100, and their bases 103 disposed adjacent to the absorbent cavity 112. This arrangement defines a series of air passages 105 that are "reversed"truncated equilateral triangles, having their bases disposed adjacent to the expiratory cavity 100, and their apexes disposed adjacent to the absorbent cavity. As such, the width of the bases of the air passages (adjacent to the expiratory cavity 100) is greater than the width of the apexes of the air passages (adjacent to the absorbent cavity 112). It has been found by the applicant that this arrangement better and more evenly distributes the patient gas in the absorbent and reduces channelling, and hence helps to increase the efficiency of the device 10.

A first solid portion 120 of the partition means is disposed generally vertically, and extends between the expiratory cavity 100 and the inspiratory cavity 106. Unlike the first grate portion 116 (which is porous), the first solid portion 120 is not permeable to gas or liquid, and prevents the flow of gas therethrough. As the first solid portion 120 does not permit the flow of gas therethrough, patient gas within the expiratory cavity 100 must flow through the right part of the absorbent cavity 112 to reach the breathing bag cavity 100.

As used in this application, the "right"part or side of the absorbent cavity 112 is that part of the cavity 112 disposed beneath the expiratory cavity 100, and the "left" part of the cavity is that portion of the cavity 112 disposed beneath the inspiratoy cavity 106 Because the inspiratory valve 42 is designed to close when the patient breathes gas through the expiratory valve 40 into the interior of the canister, the patient gas is directed through the right part of the absorbent cavity 112 (and absorbent) and into the breathing bag cavity 110. Only upon patient inspiration or squeezing of the breathing bag does the patient gas flow from the breathing bag cavity 110 via the lower and left part of the absorbent cavity and into the inspiratory cavity 106.

The second solid portion 124 of the partition means extends primarily in a generally horizontal plane which is generally parallel to (but not coplanar with) the first grate portion 116. The second solid portion 124 provides a divider between the expiratory cavity 100 and the breathing bag cavity 110. As the second solid portion 124 is not porous, it prevents the flow of gas directly from the expiratory cavity 100, into the breathing bag cavity 110. The third solid portion 128 of the partition means extends generally vertically, at an angle, and is coupled at one end to the second solid portion 124. The lower end of the third solid portion 128 terminates within the absorbent cavity 112. The third solid portion 128 is also generally solid, and does not permit the flow of gas therethrough. As such, patient gas flowing from the expiratory cavity 100, and through the first grate portion 116, must travel through at least some of the absorbent 114 held within the absorbent cavity 112 before it can enter the breathing bag cavity 110 by passing through the second grate portion 130.

The second grate portion 130 extends generally between the third solid portion 128 and the cylindrical side wall 13 of the bowl portion 14. The second grate portion 130 is constructed generally similar to the first grate portion 116, and includes a plurality of air spaces through which patient gas can flow between the breathing bag cavity 110 and the absorbent cavity 12. Similar also to first grate portion 116, second grate portion 130 should have air passages which are large enough to permit the free flow of gas therethrough, but small enough to generally retain the particles of the absorbent 114 within the absorbent cavity 112, and not permit the absorbent particles 114 to pass into the breathing bag cavity 110. In this regard, the diameter (or other largest dimension) of the air passages within the first and second grate portions 116, 130 should generally be smaller than the typical diameter of the absorbent 114 particles. Additionally, the air passages can have an inverted truncated triangular cross section, similar to the apertures 105 of the first grate portion 116.

The partition means also includes a fourth solid portion 138 that extends generally vertically, and coplanarly with the first solid portion 120. In practice, the first solid portion 120 and fourth solid portion 138 can comprise the same, generally vertical member, although that need not be the case. For purposes of this discussion, the fourth solid portion 138 is that portion having its upper end adjacent to the first and third grate portions 116, 134 and its lower end terminating within the absorbent cavity 112. The fourth solid portion 138 is asymmetrically positioned to the dispersion of gas within the absorbent 114, and to reduce channelling in the absorbent. The fourth solid portion 138 can include a fin portion 139 in the "downstream" portion of the cavity 114. The purpose of the fin portion 139 is to direct patient gas to disburse it more evenly through the absorbent, by preventing it from finding or making a relatively absorbent free channel alongside the fourth solid portion 138.

The partition means also includes a third grate portion 134 that extends generally horizontally, between the cylindrical wall 13 of the bowl portion 14, and the fourth solid portion 138. The third grate portion 134 is preferably disposed generally coplanarly with the first grate portion 116, and is constructed similarly to the first grate portion 116.

Through the various grated and solid portions of the partition means, the following gas flow pattern exists. Patient gas flows from the expiratory line 24 into the expiratory cavity 100. The patient gas 100 then flows through the first grate portion 116 into the absorbent cavity 112. Preferably, the level of absorbent 114 within the absorbent cavity 112 is comfortably full, but in any event sufficiently high so that the absorbent extends alongside the third solid portion 128, and is above second grate portion 130.

The patient gas then flows through the absorbent 114, and flows through the second grate portion 130 into the breathing bag cavity 110, and then through the breathing bag port 52, into elbow connector 54, and ultimately into breathing bag 64.

In order for the patient gas to flow into the inspiratory port 106, the patient gas must flow from the breathing bag 64 into breathing bag cavity 110, and then into the absorbent 114, past the lower terminus of the fourth solid portion 138, and around the fin portion 139. By extending downwardly into the absorbent, the fourth solid portion 138 and fin 139 force the patient gas to flow through a relatively larger amount of absorbent 114, and prevent the patient gas from bypassing the absorbent by flowing either above the level of the absorbent, or otherwise flowing through a relatively short flow path within the absorbent 114. By the time that the patient gas reaches the inspiratory cavity 106, the patient gas should be stripped of its $CO_2$. Within the inspiratory cavity 106, the patient gas can be mixed with fresh gas which is flowing through the fresh gas delivery inlet port 46. The mixed patient gas/fresh anesthesia gas can then flow through the one-way inspiratory valve 42, and out through the inspiratory port 27, and to the patient through the patient inspiratory line 30.

An overflow valve means 150 is provided for maintaining a desired patient gas pressure within the interior 41 of the canister 10, and hence within the breathing circuit of the patient. The overflow valve means 150 is best shown in FIGS. 2 and 6–10, and especially in FIG. 7, as including a valve body 152 having a downwardly and axially extending mating sleeve 154 for mating the valve body 152 to the overflow port 108 formed on the cylindrical sidewall 13 of the bowl portion 14 of the canister body 12. The valve body 152 is generally hollow, and also includes a valve housing portion 156 disposed coaxially with the mating sleeve 154. The valve housing 156 is provided for housing the valve element of the valve means 150. The valve body 152 also includes a valve outlet connector 158 which is designed for mating with a scavenging line 159 for carrying exhausted gases from the overflow valve means 150 to a waste receiving means (not shown). To comply with current standards, the valve outlet connector 158 should have a 30 mm. male taper so that it can mate properly to a female connector in a scavenging line 159. The valve outlet connector 158 includes a reduced diameter portion 160 disposed between the valve outlet connector 158 and the valve housing 156.

As best shown in FIG. 10, the valve housing 156 includes a horizontally disposed wall 164 which extends between the valve housing 156 and the mating sleeve 154. The horizontally disposed wall 164 includes a circular valve seat 168 which defines a central valve aperture 170.

The valve body 152 also includes a cap member 176 having a horizontally disposed, radially extending closure portion 178. The cap member 176 also includes a downwardly extending, circumferential flange 180 which is matable with, and frictionally received by the radially inwardly facing surface of the upper end of the valve housing 156, and bonded thereto by sonic welding or the like, to sealingly engage the cap member 176 to the valve housing 156.

Figure 6C:
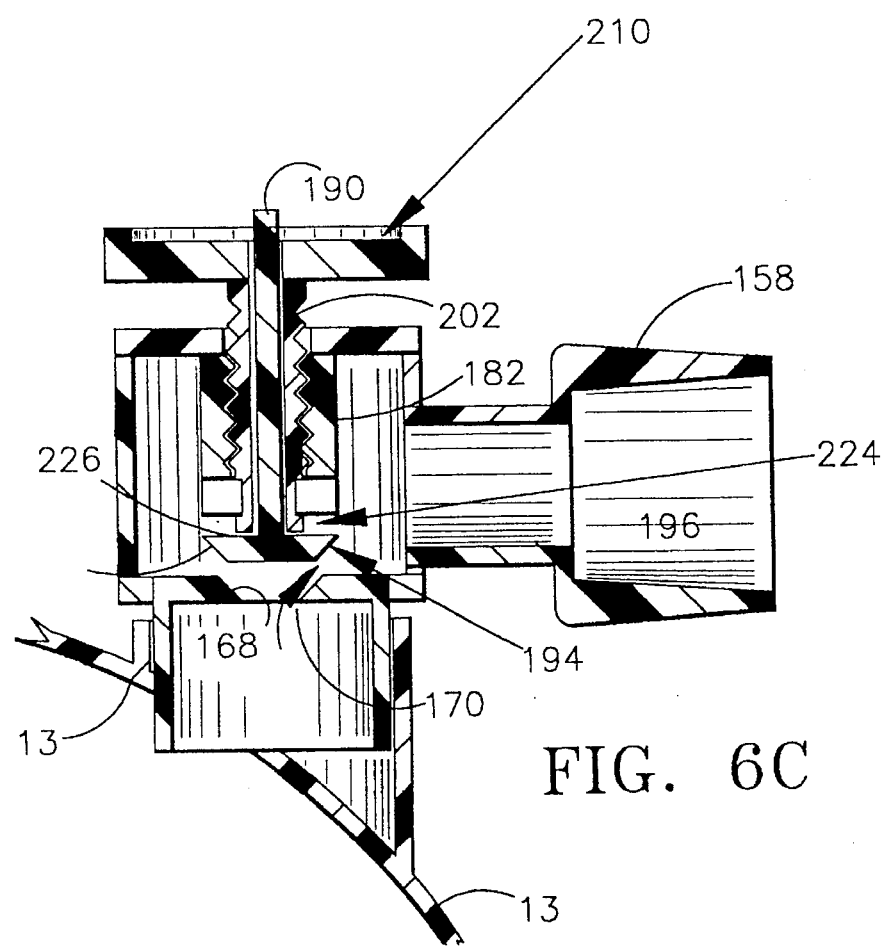
FIG. 6C is a sectional view taken along lines 6—6 of FIG. 5, showing the valve means in its valve disengaged and unlocked position.
Figure 6A:
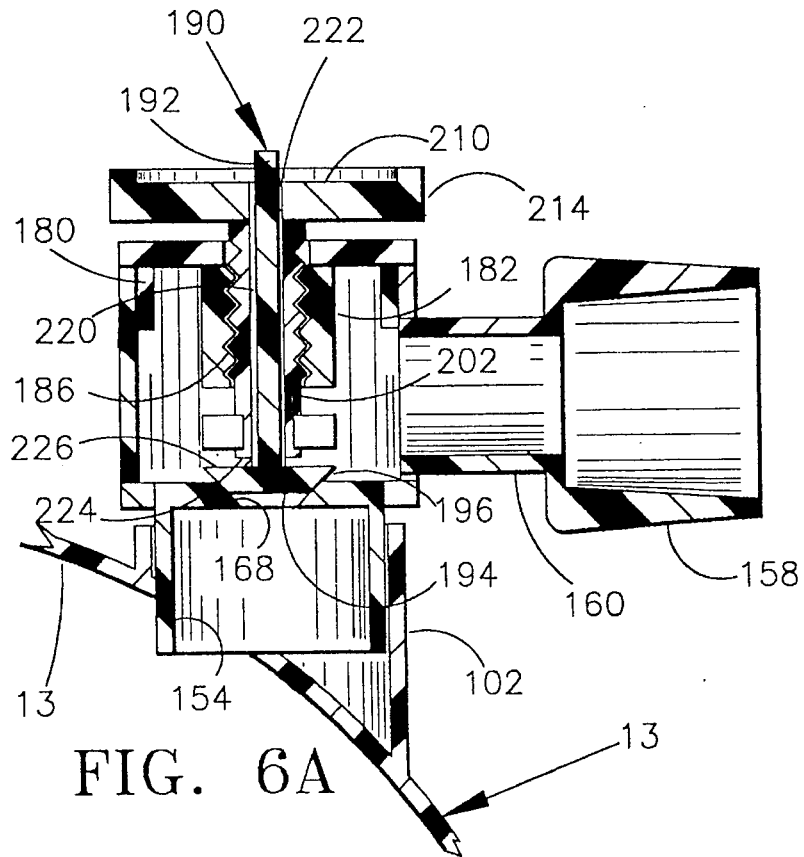
FIG. 6A is a sectional view taken along lines 6—6 of FIG. 5, showing the valve means in its valve engaged and locked position.
Figure 6B:
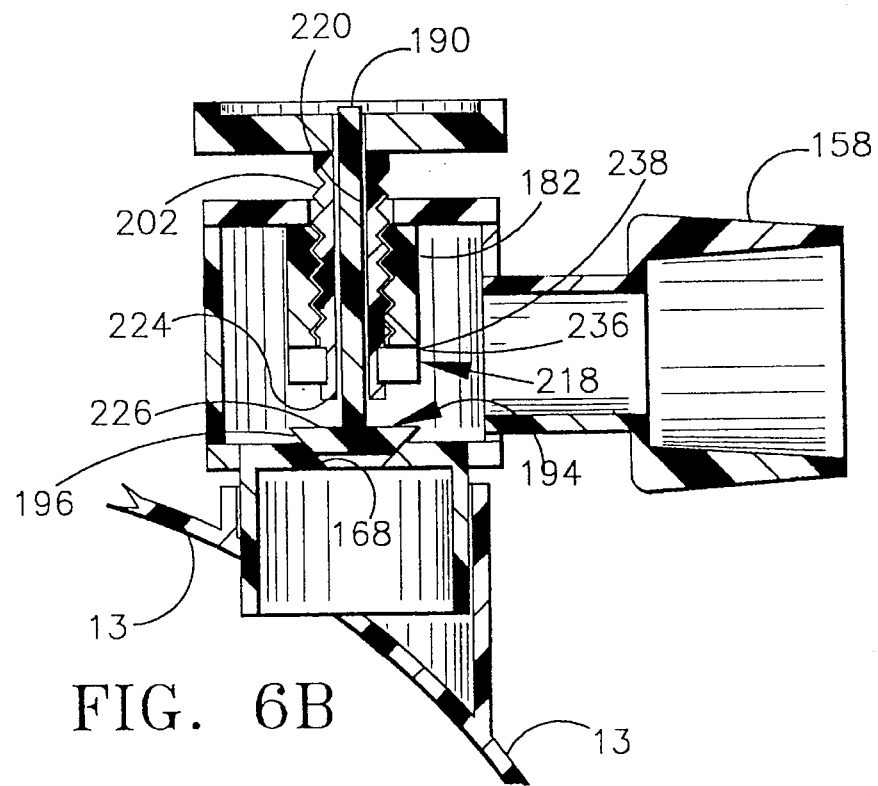
FIG. 6B is a sectional view taken along lines 6—6 of FIG. 5, showing the valve means in its valve engaged and unlocked position.
Figure 8:
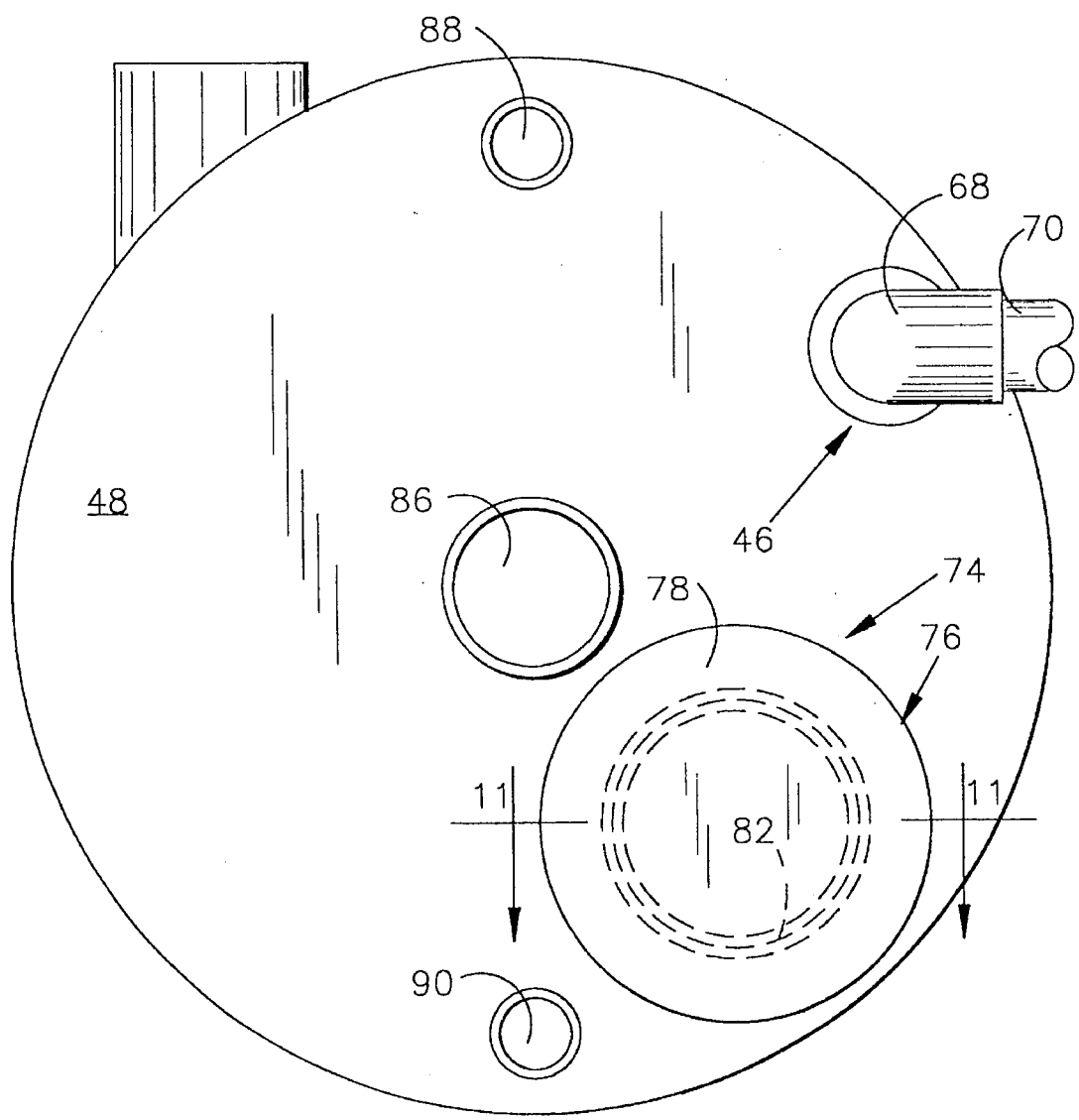
FIG. 8 is a rear view of the canister of the present invention.
Figure 11:
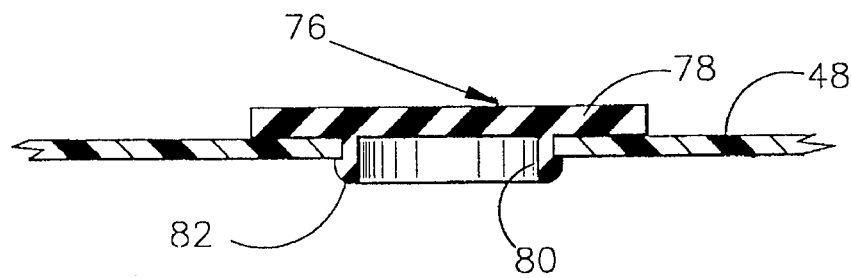
FIG. 11 is a sectional view taken along lines 11—11 of FIG. 8.

An axially extending collar member 182 is positioned centrally underneath the planar closure portion 178, and extends generally axially downwardly therefrom. As best shown in FIGS. 6A–6C, the collar member 182 includes a longitudinally extending central passageway having a threaded radially inwardly facing surface 186.

The overflow valve means 150 also includes a valve element 190, having a solid, generally cylindrical valve stem portion 192, and a radially extending valve head portion 194 disposed at the lower end of the valve stem portion 192. The valve head 194 has a radially outwardly facing, frusto-conically shaped valve seat engaging surface 196, which is provided for engaging the valve seat 168, and thereby closing the central valve aperture 170. The diameter of the valve head 194 is preferably about 11.88 mm., the length of the valve stem 192 is approximately 33.2 mm., and the weight of the valve element is approximately less than one gram. It has been found by the applicant that this particular configuration enables the valve head 194, when unlocked, to remain engaged with the valve seat 168 in slight overpressure situations (e.g., 1.0 cm $H_2O$) wherein a slight increase in pressure is built up within the interior 41 of the canister to inflate the breathing bag 64, but to pop open and allow patient gas to flow through central valve aperture 170, and out of the valve outlet connector 158 in over-pressure situations. The length of the valve stem 192 is chosen so that it protrudes about 4 mm. above the surface of the knob 210 to permit the user to grip the protruding end of the stem 192 to manually unseat the valve head 199 from the valve seat surface 168 to thereby open the valve, or to manually hold down the valve to temporarily close the valve.

The valve means 150 also includes a valve actuating means 200. The valve actuating means 200 includes a shaft member 202, having a radially outwardly facing surface which includes a threaded upper portion 204, and a smooth (non-threaded) lower surface portion 206. The smooth lower surface portion 206 includes a recessed circumferential groove 208 which is formed close to the lower end of the shaft member 202. A user actuable knob 210 is fixedly coupled to the shaft member 202, so that rotation of the knob 210 causes rotation of the shaft member 202. The knob 210 has a diameter which is preferably just slightly greater than the diameter of the closure portion 178, and includes a knurled or toothed outer surface 214 to improve the user's grip on the knob 210. A limiter member which can comprise a horseshoe shaped snap ring 218 is sized to be received within the recessed circumferential groove 208, to maintain the limiter member 218 on the shaft member 202, and to limit the axial travel of the shaft member 202, and hence the axial travel of the valve element 190.

As best shown in FIGS. 6A–6C, the shaft member 202 includes, an axially extending, centrally disposed sleeve 220 which alignable with a central aperture 222 formed in the knob 210. The sleeve 220 and central aperture 222 are provided for receiving the valve stem 192 of the valve element 190.

Turning now to FIGS. 6A–6C, it will be noted that when assembled, the valve head 194 resides axially inwardly of the shaft member 202, so that the frusto-conical valve seat engaging surface 196 of the valve head 194 can engage the valve seat 168. The valve stem 192 extends through the sleeve 220 of the shaft member 202, and the central aperture 222 of the knob 210. The valve stem 192 is sized so that it may slide freely in an axial direction within the sleeve 220 and central aperture 222.

The shaft member 202 is disposed coaxially with, and radially outwardly from the valve stem 192. The radially outwardly facing threads 204 of the shaft member 202 engage the radially inwardly facing threads 186 of the collar member 182, so that rotation of the shaft member 202 adjusts the relative axial position of the shaft member 202, through its threaded engagement with the relatively fixedly positioned collar member 182. As the shaft member 202 is fixedly coupled to knob 210, rotation of knob 210 causes rotation of shaft 202, to thereby adjust the relative axial position of the shaft member 202. The collar member 182 is dispossd coaxially with, and radially outwardly from the shaft member 202, and threadedly engages the shaft member 202.

The valve means 150 is actuable by user to move between (1) a locked position wherein the frusto-conical surface 196 of the valve head 194 is locked into engagement with the valve seat 168; and (2) an unlocked position, the valve locked position is best shown in FIG. 6A. The knob 214 is rotated in a generally clockwise direction, to cause the shaft member 202 to move axially downwardly. When so moved, the terminal, axially facing end 224 of the shaft member 202 engages the axially outwardly facing surface 226 of the valve head 194, to force the frusto-conical surface 196 of the valve head 194 into engagement with the valve seat 168. When so positioned, the engagement between the terminal surface 224, and the axially upwardly facing surface 226 prevents the valve from moving axially within the sleeve 220.

The unlocked position for the valve is best shown in FIGS. 6B and 6C. Fig. 6B shows the valve actuating means in the valve unlocked position, but shows the valve stem 192 and valve head 194 in the valve engaged position, wherein the frusto-conical surface 196 is engaged with the valve seat 168. As shown in Fig. 6B, no patient gas is permitted to flow down through the valve orifice into the interior 41 of the canister body 12, because of the engagement of the valve head 196 with the valve seat 168. However, as the valve is in its unlocked position, an over-pressure situation (or manual movement) can allow the valve element 190 to move axially upwardly, to permit the flow of gas through the valve aperture 170. FIG. 6C shows the valve element 190 as being out of engagement with the valve seat 168, to place the frusto-conical surface 196 in a valve-disengaged position. When so positioned, patient gas can flow through the valve orifice 170 to permit patient gas to flow through the valve, and out the outlet connector 158.

Turning now to FIGS. 6A–6C, the operation of a valve will now be discussed. In FIG. 6A, the valve is shown in its locked, valve engaged position. As such, the frusto-conical surface 196 is locked into engagement with the valve seat 168, by the engagement of the lower end 224 of the sleeve 202, with the axially facing upper surface 226 of the valve head 194.

Turning now to FIG. 6B, the shaft 202 is rotated in a counter-clockwise direction to its furthest upward extent. The axial travel of the shaft 202 is limited by the engagement of the axially facing upper surface 236 of the snap ring 218, and axially facing lower surface 238 of the collar 182. When the snap ring 218 is so engaged with the collar 182, the shaft 202 can not travel any further in an axially upward direction. At such time, the lower end 224 of the shaft 202 is in a spaced relationship with the upper surface 226 of the valve head 194. This permits the valve 190 to travel axially within sleeve 220.

In an over pressure situation, the valve element 190 moves axially upwardly (as shown in FIG. 6C), so that the frusto-conical surface 196 of the valve element 190 becomes disengaged from the valve seat 168. This provides a passageway through which air can travel through the valve aperture 170, and ultimately into the connector port 158. The axially upward travel of the valve element 190 is limited by the engagement of the upper surface 226 of the valve head 194 with the lower end of the shaft member 202.

Because of the threaded engagement between the collar 182 and the shaft member 202, the potential travel of the valve element 190 is infinitely adjustable by the user. Although the valve is shown at its fully closed position in FIG. 6B, and its fully open position in FIG. 6C, it will be appreciated that the user can rotate knob 210 to cause the collar member 202 to be positioned intermediate the positions shown in FIGS. 6A and 6C. Through this adjustment, the user can adjust the potential flow rate of patient gas through the aperture 170.

Having described the invention in detail with reference to certain preferred embodiments, it will be appreciated that certain variations and modifications are possible within the scope and spirit of the appended claims.

What is claimed is:

1. A canister for use with an anesthesia and resuscitation machine, the canister including a canister body defining an interior for holding a carbon dioxide absorbent material, a unidirectional expiratory valve integrally mounted to the canister body through which a patient gas can pass into the canister body interior, a unidirectional inspiratory valve integrally mounted to the canister body through which the patient gas can pass out of the canister body interior, an overflow orifice extending through the canister body, through which the patient gas can pass, and a unidirectional overflow valve means coupled to the overflow orifice for permitting a controlled flow of patient gas therethrough to maintain a desired gas pressure within the interior of the canister body, the valve means being biased by gravity into a valve engaged position to normally prevent the flow of patient gas therethrough and being movable, against the influence of gravity, if an over-pressure situation occurs with the interior of the canister body.

2. The device of claim 1 wherein the canister body includes (1) a generally planar front surface and a generally planar rear surface, and at least one of the unidirectional inspiratory valve and expiratory valve are integrally mounted to the canister body between said front surface and rear surface;

(2) an inspiratory port, to which an inspiratory line can be attached; and (3) an expiratory line to which an expiratory line can be attached, expiratory port including a key means to prevent connection of a male gas line connector thereto.

3. The device of claim 1 wherein the canister body includes (a) a bowl portion (b) a lid portion sealingly engagable with the bowl portion, and (c) a partition means for defining an expiratory cavity, an inspiratory cavity disposed adjacent the expiratory cavity, and an absorbent cavity in which the absorbent can be placed, the partitions defining a patient gas flow path from the expiratory valve, into the expiratory cavity, through the absorbent cavity, through the inspiratory cavity, and then through the inspiratory valve.

4. The device of claim 3 wherein the overflow orifice is disposed adjacent to the expiratory cavity, further comprising a fresh gas orifice disposed adjacent to the inspiratory cavity.

5. The device of claim 1 wherein the overflow valve means includes (1) a valve member, and (2) a valve seat defining a valve aperture through which the patient gas can pass out of the interior of the body.

6. The device of claim 5 wherein the overflow valve means includes a valve actuating means for adjusting the valve between (1) a locked position wherein the valve member is locked into the valve engaged position wherein the valve member is engaged with the valve seat to prevent the flow of patient gas through the valve aperture, and (2) an unlocked position wherein the valve member can move, under the influence of patient gas pressure, between the valve engaged position, and a valve disengaged position wherein the valve member is disposed in a spaced relation to the valve seat to permit the patient gas to flow through the valve aperture.

7. The device of claim 6 wherein (1) the canister means includes a breathing bag port to which a breathing bag can be attached for placing the breathing bag in fluid communication with the interior of the canister body, and (2) the valve member is sized and weighted to remain, under the influence of gravity, when in the unlocked position, in the valve engaged position until the pressure of the patient gas within the interior of the canister body is sufficient to cause the inflation of the breathing bag.

8. The device of claim 6 wherein the valve member includes a stem portion and a head portion, and the valve actuating means includes:

(1) a collar member having a threaded surface, (2) a shaft member having a threaded surface for engaging the threaded surface of the collar member, and a sleeve portion for slidably receiving the stem portion of the valve member.

9. The device of claim 8, wherein the shaft member includes a limiter member for limiting the travel of each of the shaft member and the valve member, and for maintaining the shaft member in engagement with the collar member.

10. The device of claim 9, wherein the shaft member includes a recessed groove disposed between the collar member and the valve head portion, and the limiter member comprises a snap ring receivable in the recessed groove, the snap ring being engagable with the collar member for limiting the travel of the shaft member.

11. The device of claim 6 wherein the valve member is adjustable to permit a variable flow rate through the aperture, and wherein when the valve is in its unlocked position, the valve member is normally biased into the valve engaged position.

12. The device of claim 11 wherein (1) the canister means includes a breathing bag port to which a breathing bag can be attached, for placing the breathing bag in fluid communication with the interior of the canister body, and (2) the valve member is sized and weighted to remain, when in the unlocked position, in the valve engaged position, until the pressure of the patient gas within the interior of the canister body is sufficient to cause the inflation of the breathing bag.

13. The device of claim 12 wherein the overflow valve member includes a stem portion and a head portion, and the valve actuator means includes (1) a collar member having a threaded surface, (2) a shaft member having a threaded surface for engaging the threaded surface of the collar member, and a sleeve portion for slidably receiving the stem portion of the valve member.

14. The device of claim 13 wherein the valve actuating means includes a knob member fixedly coupled to the shaft member for rotating the shaft member, the knob member including an aperture aligned with the sleeve portion for slidably receiving the stem portion of the valve member.

15. The device of claim 14 wherein the shaft member includes a limiter member for limiting the travel of each of the shaft member, and the valve member, and for maintaining the shaft member in engagement with the collar member.

16. The device of claim 15 wherein the shaft member includes a recessed groove disposed between the collar member and the valve head portion, and the limiter member comprises a snap ring receivable in the recessed groove, the snap ring being engagable with the collar member for limiting the travel of the shaft member.

17. A canister for use with an anesthesia and resuscitation machine, the canister including a canister body defining an interior for holding a carbon dioxide absorbent material, a unidirectional expiratory valve integrally mounted to the canister body through which a patient gas can pass into the canister body interior, a unidirectional inspiratory valve integrally mounted to the canister body through which the patient gas can pass out of the canister body interior, an overflow orifice extending through the canister body, through which the patient gas can pass, the overflow orifice being disposed adjacent to the expiratory cavity, a fresh gas orifice disposed adjacent to the inspiratory cavity, a unidirectional overflow valve means coupled to the overflow orifice for permitting a controlled flow of patient gas therethrough to maintain a desired gas pressure within the interior of the canister body, the valve means being biased by gravity into a valve engaged position to normally prevent the flow of patient gas therethrough, the overflow valve means including:

(1) valve member including a stem portion and a head portion, and (2) valve seat defining a valve aperture through which the patient gas can pass out of the interior of the body (3) valve actuating means for adjusting the valve between a locked position wherein the valve member is locked in a fixed position, and an unlocked position wherein the valve member can move, the valve actuating means including:

(a) a collar member having a threaded surface, (b) a shaft member having a threaded surface for engaging the threaded surface of the collar member, and a sleeve portion for slidably receiving the stem portion of the valve member, and (4) a cap means for engaging a surface of the outlet orifice, wherein the collar member is fixedly coupled to the cap means, the threaded surface of said collar member comprises a threaded radially inwardly facing surface, the threaded surface of the shaft member comprises a threaded radially outwardly facing surface, and the sleeve portion comprises a longitudinally extending central passageway formed in the shaft portion.

18. The device of claim 17 wherein the valve member includes a knob member fixedly coupled to the shaft member for rotating the shaft member to induce vertical travel of the shaft member.

19. A canister for use with an anesthesia and resuscitation machine, the canister including a canister body defining an interior for holding a carbon dioxide absorbent material, a unidirectional expiratory valve integrally mounted to the canister body through which a patient gas can pass into the canister body interior, a unidirectional inspiratory valve integrally mounted to the canister body through which the patient gas can pass out of the canister body interior, an overflow orifice extending through the canister body, through which the patient gas can pass, the overflow orifice being disposed adjacent to the expiratory cavity, a fresh gas orifice disposed adjacent to the inspiratory cavity, a unidirectional overflow valve means coupled to the overflow orifice for permitting a controlled flow of patient gas therethrough to maintain a desired gas pressure within the interior of the canister body, the valve means being biased by gravity into a valve engaged position to normally prevent the flow of patient gas therethrough, the canister body including
(1) a bowl portion
(2) a lid portion sealingly engagable with the bowl portion, and
(3) partition means for defining an expiratory cavity, an inspiratory cavity disposed adjacent the expiratory cavity, and an absorbent cavity in which the absorbent can be placed, the partitions defining a patient gas flow path from the expiratory valve, into the expiratory cavity, through the absorbent cavity, through the inspiratory cavity, and then through the inspiratory valve, the partition means further defining a breathing bag cavity in fluid communication with the absorbent cavity, and a breathing bag port orifice in fluid communication with the breathing bag cavity, the breathing bag port orifice being capable of receiving a breathing bag means, and being placed in the patient gas flow both downstream and upstream of the absorbent cavity.

20. The device of claim 18 wherein the partition means includes at least one grate portion through which the patient gas can pass from one of the absorbent and breathing bag cavity into the absorbent cavity, the one grate portion including a first surface, a second surface disposed adjacent the absorbent cavity, and a series of apertures extending between the first and second surfaces, the apertures each having a first opening at the first surface, and a second opening at the second surface, said second openings being smaller than said first openings.

21. The device of claim 19 wherein the partition means comprises
(a) a first grate portion disposed between the expiratory cavity and the absorbent cavity,
(b) a first solid portion disposed the expiratory cavity and the inspiratory cavity,
(c) a second solid portion disposed between the expiratory cavity and the breathing bag cavity,
(d) a third solid portion disposed between the breathing bag cavity and the absorbent cavity,
(e) a second grate portion disposed between the breathing bag cavity and the absorbent cavity,
(f) a third grate portion disposed between the absorbent cavity and the inspiratory portion, and
(g) a fourth solid portion disposed generally between the first and third grate portions, and extending into the absorbent cavity for directing the flow of patient gas through the first grate portion to flow in the absorbent cavity, and around the fourth solid portion before passing through the third grate portion.

22. A canister for use with an anesthesia and resuscitation machine, the canister including a canister body defining an interior for holding a carbon dioxide absorbent material, a unidirectional expiratory valve integrally mounted to the canister body through which a patient gas can pass into the canister body interior, a unidirectional inspiratory valve integrally mounted to the canister body through which the patient gas can pass out of the canister body interior, an overflow orifice extending through the canister body, through which the patient gas can pass, and a unidirectional overflow valve means coupled to the overflow orifice for permitting a controlled flow of patient gas therethrough to maintain a desired gas pressure within the interior of the canister body, the valve means being biased by gravity into a valve engaged position to normally prevent the flow of patient gas therethrough the overflow valve means including:
(1) a valve member,
(2) a valve seat defining a valve aperture through which the patient gas can pass out of the interior of the body, and
(3) a mechanical valve actuating means for enabling the valve member to be placed in both:
(a) a locked position wherein the valve member is locked into the valve engaged position wherein the valve member is engaged with the valve seat to prevent the flow of patient gas through the valve aperture, and
(b) an unlocked position wherein the valve member can move, under the influence of patient gas pressure, between the valve engaged position, and a valve disengaged position wherein the valve member is disposed in a spaced relation to the valve seat to permit the patient gas to flow through the valve aperture.

* * * * *